United States Patent
Dong et al.

(10) Patent No.: US 11,427,809 B2
(45) Date of Patent: Aug. 30, 2022

(54) METHODS FOR ISOLATING ADENO-ASSOCIATED VIRUS USING A POLYDIALKYLAMMONIUM SALT

(71) Applicant: LONZA HOUSTON INC., Houston, TX (US)

(72) Inventors: Wenling Dong, Katy, TX (US); Anandita Seth, Katy, TX (US); Robert J. Milczarek, Katy, TX (US); Francesca P. Vitelli, Houston, TX (US)

(73) Assignee: LONZA HOUSTON, INC., Houston, TX (US)

( * ) Notice: Subject to any disclaimer, the term of this patent is extended or adjusted under 35 U.S.C. 154(b) by 905 days.

(21) Appl. No.: 16/303,545

(22) PCT Filed: May 25, 2017

(86) PCT No.: PCT/US2017/034389
§ 371 (c)(1),
(2) Date: Nov. 20, 2018

(87) PCT Pub. No.: WO2017/205573
PCT Pub. Date: Nov. 30, 2017

(65) Prior Publication Data
US 2020/0407695 A1     Dec. 31, 2020

Related U.S. Application Data

(60) Provisional application No. 62/341,520, filed on May 25, 2016.

(51) Int. Cl.
| | | |
|---|---|---|
| *C12N 15/10* | (2006.01) | |
| *C12N 15/11* | (2006.01) | |
| *C12N 9/22* | (2006.01) | |
| *C12N 15/85* | (2006.01) | |
| *C12N 15/113* | (2010.01) | |
| *C12N 7/00* | (2006.01) | |

(52) U.S. Cl.
CPC ...... *C12N 7/00* (2013.01); *C12N 2750/14143* (2013.01); *C12N 2750/14151* (2013.01)

(58) Field of Classification Search
CPC .... C12N 2310/20; C12N 9/22; C12N 15/113; C12N 15/85; C12Q 1/6816
See application file for complete search history.

(56) References Cited

U.S. PATENT DOCUMENTS

2013/0158247 A1     6/2013   Fabis et al.

FOREIGN PATENT DOCUMENTS

| | | |
|---|---|---|
| CN | 1189104 A | 7/1998 |
| CN | 101453889 A | 6/2009 |
| FR | 3002948 A1 | 9/2014 |
| JP | 2001-327283 A | 11/2001 |
| JP | 2016-025852 A | 2/2016 |
| KR | 2016-0044887 A | 4/2016 |
| WO | 97/08298 | 3/1997 |
| WO | 99/11764 | 3/1999 |
| WO | 99/11764 A2 | 3/1999 |
| WO | 00/14205 | 3/2000 |
| WO | 2014/135593 A1 | 9/2014 |
| WO | WO2014135593 * | 9/2014 |
| WO | 2015/038625 A1 | 3/2015 |
| WO | 2016/004319 A1 | 1/2016 |

OTHER PUBLICATIONS

Grieger, Joshua C. et al., "Production of Recombinant Adeno-associated Virus Vectors Using Suspension HEK293 Dells and Continuous Harvest of Vector From the Culture Media for GMP FIX and FLT1 Clinical Vector," Molecular Therapy 24(2):287-297 (2016); published online Nov. 3, 2015.
Mcnerney, Thomas et al., "PDADMAC flocculation of Chinese hamster ovary cells: Enabling a centrifuge-less harvest process for monoclonal antibodies," mAbs 7(2):413-427 (2015); published online Feb. 23, 2015.
International Search Report dated Aug. 24, 2017 in corresponding International Patent Application No. PCT/US2017/034389.
Extended European Search Report, dated Sep. 19, 2019 in EP 17803551.
Liu et al., Polymer Bulletin, 2006, 5:86-93.
Zhou et al., "PEG-modulated column chromatography for purification of recombinant adeno-associated virus serotype 9," Journal of Virological Methods, 2011, 173(1):99-107.

* cited by examiner

*Primary Examiner* — Barry A Chestnut
(74) *Attorney, Agent, or Firm* — Medler Ferro Woodhouse & Mills PLLC

(57) ABSTRACT

The invention relates to methods of selectively purifying an adeno-associated virus (AAV) from an aqueous biomass using a flocculent. In embodiments, the flocculent is polydiallyldialkylammonium salt, e.g., polydiallyldimethylammonium chloride (pDADMAC).

20 Claims, 4 Drawing Sheets

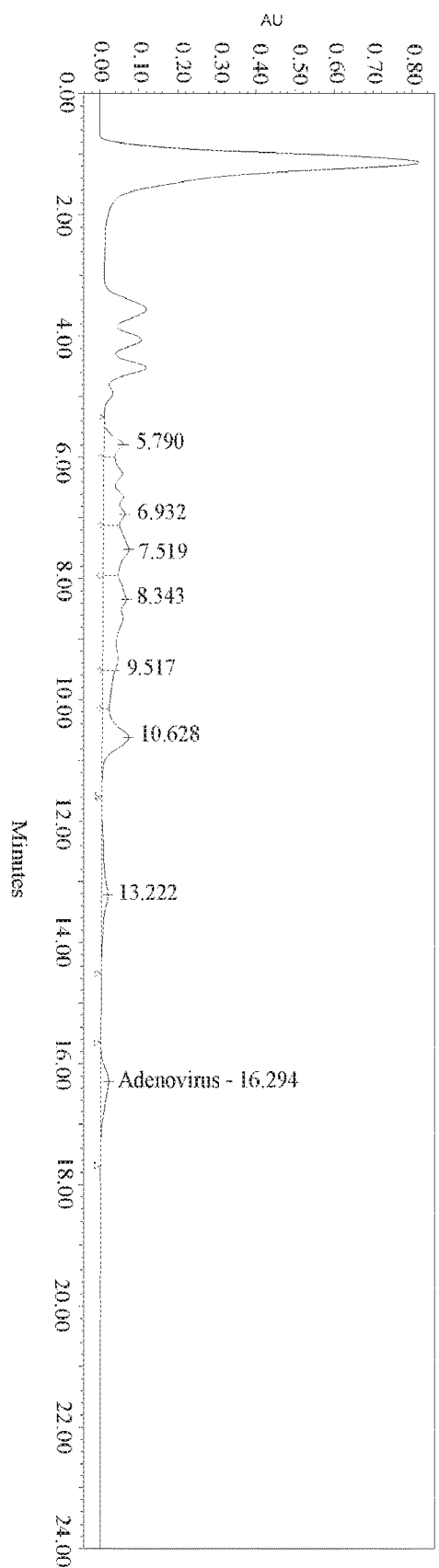
FIG. 1 HPLC Profile for Clarisolve Filtrate, no pDADMAC

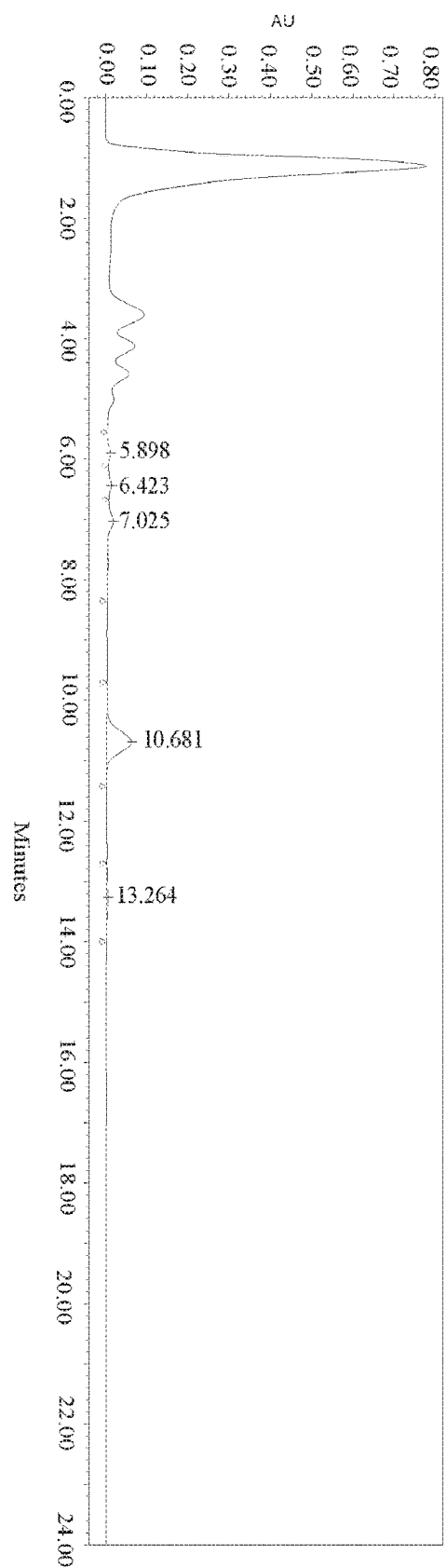
FIG. 2 HPLC Profiles for Clarisolve Filtrate, with 0.025% pDADMAC

FIG. 3 HPLC Profile for Cell Lysate Supernatant, Effect of pDADMAC at 0.01% and 0.025%
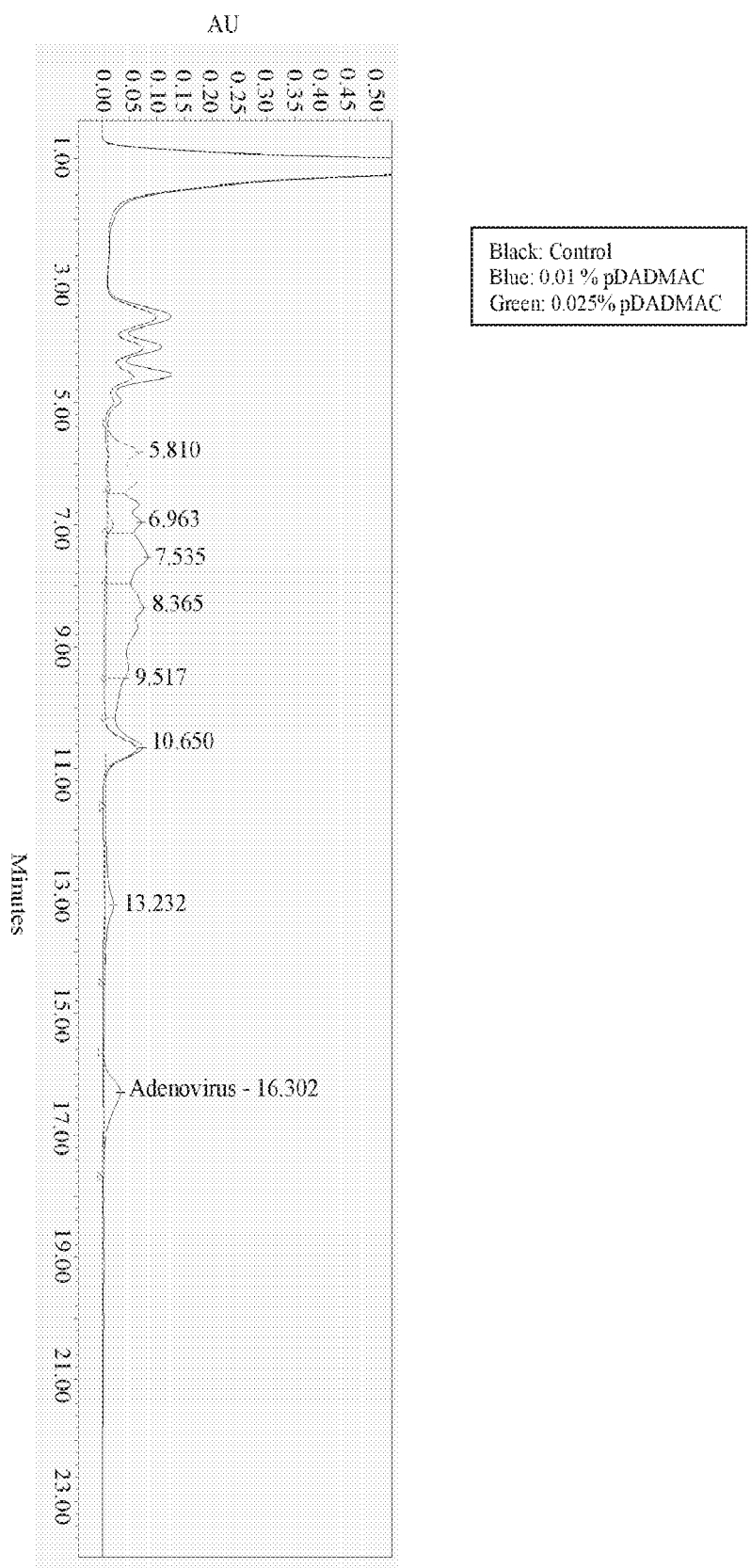

FIG. 4 HPLC Profile for Cell Lysate Supernatant, Effect of pDADMAC at 0.05% and 0.1%
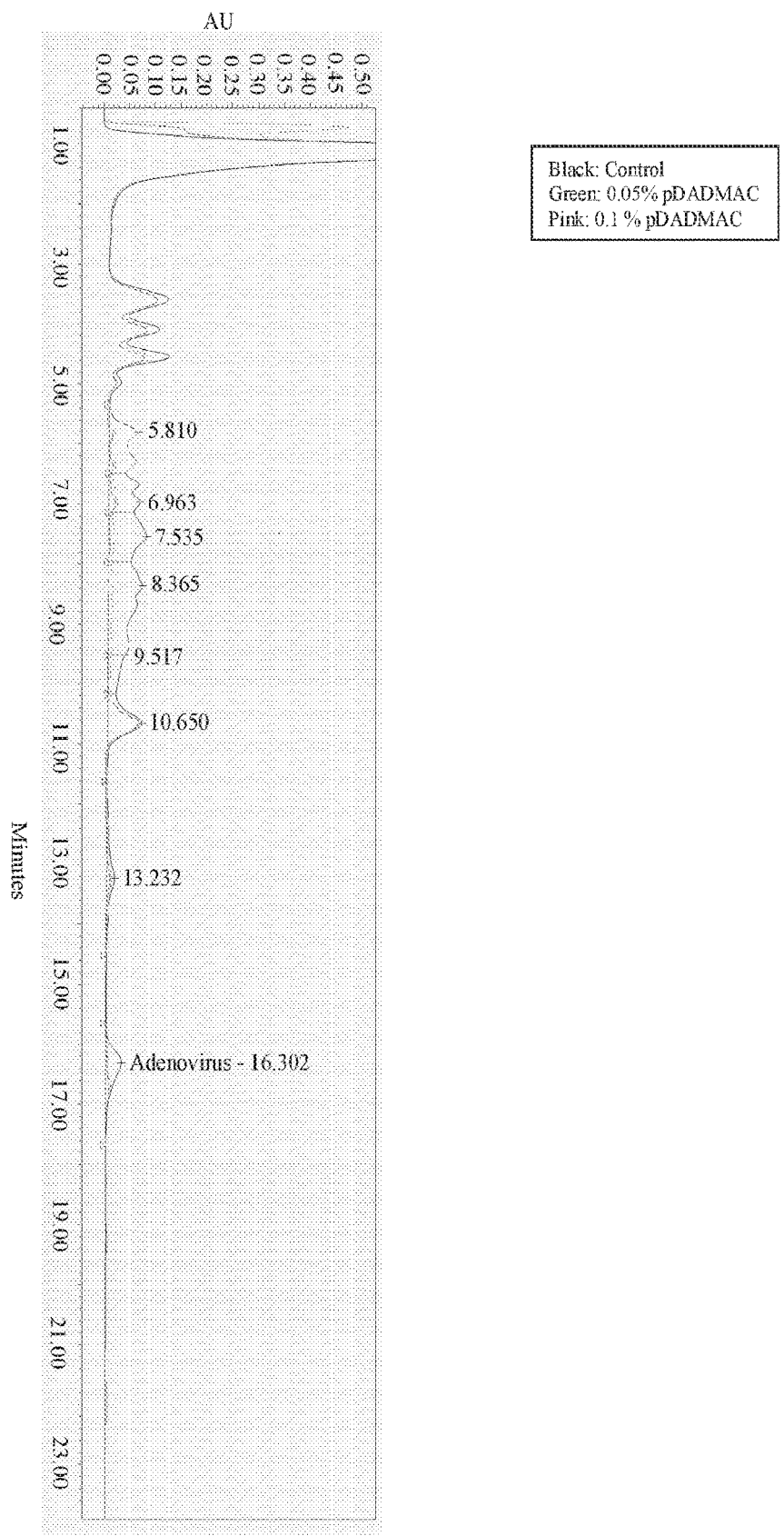
Black: Control
Green: 0.05% pDADMAC
Pink: 0.1 % pDADMAC

METHODS FOR ISOLATING ADENO-ASSOCIATED VIRUS USING A POLYDIALKYLAMMONIUM SALT

FIELD OF INVENTION

The invention relates to methods of selectively purifying an adeno-associated virus (AAV) from an aqueous biomass using a flocculent. In embodiments, the flocculent is polydiallyldialkylammonium salt, e.g., polydiallyldimethylammonium chloride (pDADMAC).

BACKGROUND OF THE INVENTION

Adeno-associated virus (AAV) is a helper-virus-dependent parvovirus used as a vector in gene therapy because of its ability to transduce dividing and non-dividing cells, its low immunogenicity, and its ability to generate AAV serotypes with broad or narrow tissue specificity. Of the many successful tissue culture and small animal studies using recombinant adeno-associated virus (rAAV) vectors, few have advanced to clinical trials. Preclinical efficacy testing, especially in large animal models and toxicology studies, requires vector quantities not easily produced in laboratory and most research-grade vector core facilities.

AAV has shown stable and efficacious gene transfer in clinical studies. Increasing interest in AAV drives the need to improve large-scale vector production for clinical supply. One of most scalable ways to generate AAV gene therapy products is by using recombinant producer cell lines Which produce essential genetic elements required to assemble AAV, such as replicase and capsid protein encoding sequences as well as the target transgene of interest. These genetic elements and transgenes of interest have been stably transfected into permissive host cell lines. However, in order to trigger packaging and release of AAV, AAV-helper viruses encoding regions such as E1, E1a and E4 are needed, requiring infection of the producer cell line with AAV-helper viruses. Although this process is very robust, and generates over 80% full AAV capsids containing the target transgene, in order to ensure safety, purity and quality of the AAV product, AAV-helper virus must be fully cleared during subsequent purification steps. In order to address this critical step, current industry standard relies on chromatography, viral clearance filters and heat inactivation individually or in combination.

SUMMARY OF THE INVENTION

In embodiments, the invention provides a method of purifying adeno-associated virus (AAV) from an aqueous biomass containing said adeno-associated virus and at least one AAV-helper virus, comprising: (a) contacting said biomass with a polydiallyldialkylammonium salt to form an aggregate and a clarified solution, wherein said aggregate comprises said at least one AAV-helper virus, (b) removing said aggregate from the clarified solution, and (c) further isolating the AAV from the clarified solution.

In embodiments, the invention further provides a method of isolating an adeno-associated virus (AAV) containing a target transgene, comprising: (a) transfecting a producer cell with the AAV and an AAV-helper virus to produce transfected producer cell; (b) culturing said transfected producer cell; (c) lysing said transfected producer cell to create an aqueous biomass; (d) introducing polydiallyldialkylammonium salt into said biomass to produce an aggregate comprising said AAV-helper virus and a clarified solution comprising the AAV; and (e) contacting said clarified solution with a purification column to produce isolated AAV.

In embodiments, the invention further provides a method of isolating an adeno-associated virus (AAV) containing a target transgene, comprising: (a) transfecting a producer cell with the AAV and an AAV-helper virus to produce transfected producer cell; (b) culturing said transfected producer cell to produce an aqueous biomass; (c) introducing polydiallyldialkylammonium salt into said biomass; and (d) processing said clarified solution with a purification column to produce isolated AAV.

DESCRIPTION OF THE FIGURES

FIG. 1: Analytical HPLC chromatography profile for Clarisolve lysate: no pDADMAC (control): Ad5 peak detected at expected retention time about 16 minutes.

FIG. 2: Analytical HPLC chromatography profile for Clarisolve lysate (with pDADMAC), no Ad5 virus peak at expected retention time about 16 minutes.

FIG. 3: Analytical HPLC chromatography profile for lysates: Effect of pDADMAC at 0.01% and 0.025%; Ad5 peak detected at expected retention time about 16 minutes for the control sample, but not for samples treated with pDADMAC at 0.01% and 0.025%.

FIG. 4: Analytical HPLC chromatography profile for lysates: Effect of pDADMAC at 0.05% and 0.1%; Ad5 peak detected at expected retention time about 16 minutes for the control sample, but not for samples treated with pDADMAC at 0.05% and 0.1%.

DETAILED DESCRIPTION

The present invention provides a method of purifying adeno associate viruses (AAV) from at least one AAV-helper virus in an aqueous biomass containing the AAV virus and the AAV-helper virus. In some embodiments, the invention provides contacting the biomass with polymer comprising a strong cationic and activated-adsorbent group radical, e.g., polydiallyldimethylammonium chloride (pDADMAC), to form an aggregate that contains the AAV-helper virus, and removing the aggregate to form a clarified solution. Once the aggregate is removed, the remaining clarified solution contains the AAV substantially free of the helper virus, and the filtrate can then be subjected to chromatography to further isolate the AAV.

Various polymers containing a strong cationic and activated-adsorbent group can be used as a selective flocculant according the present invention. In some embodiments, the polymer is a polydiallyldialkylammonium salt, e.g., a polydiallyldialkylammonium fluoride, chloride, or bromide. In some embodiments, the polymer is a polydiallyldimethylammonium salt, a polydiallyldiethylammonium salt, or a polydiallyldipropylammonium salt, for example polydiallyldimethylammonium chloride, polydiallyldimethylammonium fluoride, or polydiallyldimethylammonium bromide. In some embodiments, the polymer is polydiallyldimethylammonium chloride. Polydiallyldimethylammonium chloride (pDADMAC) is a water soluble polycationic homopolymer with a large molecular weight. The polymer body contains strong cationic and activated-adsorbent group radicals that can destabilize and flocculate any suspended solids and negatively-charged water soluble matter in a liquid while minimizing flocculation of AAV. While not being bound by any particular theory, when used in an appropriate concentration, polydiallyldialkylammonium salt, e.g., pDADMAC, rapidly flocculates the negatively charged cells and cellular debris into larger particles via an ionic interaction mechanism (electro-neutralization and bridging adsorption), enabling efficient, simple separation and removal. Polydiallyldialkylammonium salts, e.g., pDADMAC, have previously been shown to be effective in decoloring liquids, and in coagulating and flocculating inorganic and organic particles such as silt, clay, algae, bacteria and viruses in several industries such as effluent treatment, water treatment and papermaking. However, the present invention is the first to demonstrate polydiallyldialkylammonium salts can selectively flocculate other AAV-helper viruses, while not substantially flocculating AAV, thereby providing a method for selectively purifying AAV from AAV-helper viruses.

Various concentrations of polydiallyldialkylammonium salt can be used according to the present invention. In embodiments, the biomass is a cell lysate and the polydiallyldialkylammonium salt, e.g., pDADMAC, is added to the biomass at a concentration of about 0.01% to about 0.5%, or about 0.025% to about 0.1% (w/v). In some embodiments, the polydiallyldialkylammonium salt, e.g., pDADMAC, concentration is 0.025%, 0.03%, 0.035%, 0.04%, 0.05%, 0.07%, 0.08%, 0.09%, 0.1%, 0.2%, 0.3%, 0.4%, or 0.5% (w/v).

Adeno-associated viruses (AAV) include small, replication-defective, non-enveloped viruses of the genus *Dependoparvovirus*, which in turn belongs to the family *Parvoviridae* (parovovirus). In some embodiments, the AAV is a recombinant AAV (rAAV). Throughout the present application, the term AAV can be replaced with rAAV if appropriate. In some embodiments, the rAAV comprises a transgene. AAVs are dependent on an AAV helper-virus for propagation. In some embodiments, the AAV is active. The term "active" refers to the ability of the AAV to form a titer when plated.

AAV production has evolved since the first reported use of AAV as a transducing vector, however, the basic requirements remain unchanged. All current AAV production methods require a common set of factors acting in trans with respect to the vector genome. In some embodiments these components consist of the AAV non-structural proteins, the AAV structural proteins, a set of helper-virus gene products and cellular factors necessary for macromolecular syntheses, including DNA polymerase components for vector genome replication. Both the AAV genome and vector genome are linear, single-stranded DNA with interrupted terminal palindromes, usually referred to as inverted terminal repeats (ITRs). The ITRs are the only cis element required for AAV DNA rescue from a duplex form and subsequent replication, packaging and possibly for stabilizing the vg in the transduced cell.

AAV-helper viruses, provide additional trans-acting factors required for productive AAV infection in mammalian cells. In some embodiments, the AAV-helper virus is selected from the group comprising adenovirus, herpes simplex virus and baculovirus.

The same set of adenovirus gene products necessary for AAV infection is also required for efficient recombinant AAV (rAAV) production. The adenovirus genes providing AAV helper-viruses can provide E1a, E1b55k, E4orf6, E2a and VA RNA. In addition to enhancing the promoter activation of other cellular genes. E1A also has a well-defined role in the regulation transcriptional activator/repressor protein YY1.

Various cells can be used in the production of AAV. For example, in some embodiments, AAV can be produced in a mammalian cell. In some embodiments, AAV can be produced in an insect cell. In some embodiments, the AAV can be produced in a HeLa cell. In some embodiments, the cells used for AAV production, i.e., "producer cells," are HeLa cells, human embryonic kidney cells, such as HEK293, and insect cells, such as *Spodoptera frugiperda* (Sf9) cells. In some embodiments, the producer cells are HEK293 cells. In some embodiments, the producer cells are Sf9 cells. In some embodiments, the cells can be any other type of mammalian cells, including CHO, Per.C6. In some embodiment, helper virus is required.

In some embodiments, AAV is produced using HEK 293 cells chemically co-transfected with plasmids encoding the necessary virus proteins and the viral genome. However, the absence of cell-to-cell transmission limits AAV production to cells initially transfected with plasmid DNAs and perhaps retained in sufficient copy number in daughter cells. Because plasmids are typically incapable of replication in mammalian cells, the copy numbers of the rep and cap genes are not geometrically expanded. Similarly, in some embodiments, the adenovirus helper genes are introduced into the HEK 293 cells as non-infectious plasmids, and the helper gene dosages remain constant during production.

Scaling up AAV production basically requires increasing the cell number in a manner compatible with the upstream production process. AAV production typically is performed on adherent cells or suspension cultures.

For chemical transfection-based processes, adherent cells are typically grown as monolayers in plastic cell culture plates or roller bottles. The available surface area determines the maximum number of cells and, therefore, the amount of AAV produced.

Alternatively, suspension cultures allow cell expansion based on volume rather than area. The conversion factor for adherent cell number to suspension cell number can be about 10-50 $cm^2$=1 $cm^3$, depending on cell density for either format. Transfection methods for producing AAV using either inorganic compounds, e.g. calcium phosphate, or organic compounds, e.g. polyethyleneimine (PEI), or non-chemical, e.g. electroporation, have been extensively described using adherent cells. However, for suspension cells, transfection using either calcium phosphate or PEI is most commonly used. PEI is often used, presumably due to the reproducibility and reliability of using a commercially available, single reagent rather than the more complicated (and idiosyncratic) calcium phosphate transfection procedure.

In some embodiments, the AAV-helper virus is a baculovirus expression vector, used for producing AAV in *Spodoptera frugiperda* (Sf9) cells. First, the recombinant baculovirus initiates a productive infection and subsequently the progeny baculovirus can secondarily infect additional cells in the culture. With about 100 infectious baculovirus particles released per cell, the entire cell culture population becomes infected within one or two infection cycles depending on the initial multiplicity of infection. In some embodiments, Sf9 host cells replicate the vector DNA much more efficiently than HEK 293 cells. Additionally, the baculovirus can provide the insect cells with sequences required for AAV structural protein production, viral assembly and packaging of the transgene.

In some embodiments, the physical, biochemical and biological characteristics of Sf9 cell-produced AAV indicate that AAV produced in Sf9 cells is equivalent to AAV produced in HEK 293 cells. Analysis of vector-derived genomes demonstrated that up to 4.7 kb of linear, single-stranded DNA is efficiently packaged.

In broad terms, recovery of AAV from an aqueous cell culture biomass involves (i) liberating AAV from cells if needed, (ii) separating AAV from other cell debris and media components and (iii) concentrating and purifying the AAV. The AAV capsids are resilient and robust; therefore, downstream processes can exploit conditions that are otherwise avoided, such as prolonged exposure to elevated temperatures, repeated freezing and thawing cycles, acidic conditions and exposure to organic solvents. However, care must be taken to not co-isolate other viruses, e.g., AAV-helper viruses, when recovering the AAV.

The initial steps in downstream processing are determined in part by the cell culture format. Adherent cells may be lysed in situ or detached from the growth substrates and lysed in a small, disposable vessel by freeze-thaw lysis, mechanical homogenization or chemically via the use of surfactants. Large volume suspension cultures may be treated with surfactants, e.g. Triton X-100, Tween 20, or homogenized with a mechanical device. Nuclease treatment, e.g., benzonase treatment, may be incorporated following lysis to reduce DNA contaminants and facilitate subsequent filtration and chromatography steps.

In some embodiments when AAV is produced using Ad helper virus, following cell lysis, the lysed cell biomass can be flocculated by the addition of a polydiallyldialkylammonium salt, e.g., pDADMAC. The aggregates of cell components can be removed either by filtration (convenient for large volumes) or centrifugation, leaving the AAV substantially in the clarified biomass solution. In some embodiments, a series of filters with decreasing pore sizes are used to prevent clogging by cellular components. In some embodiments, tangential flow filtration (TFF) is used. In embodiments, the aggregate formed by biomass flocculation is removed via filtration, for example using Clarisolve filtration. Most of the flocculent and aggregates are removed by filtration and residual flocculent can be removed in subsequent chromatography steps. In embodiments, a viral clearance filter such as Viresolve is used in combination with the methods of the invention to isolate AAV. In some embodiments, analytical techniques, e.g., HPLC, PCR, and/or bioassay can be used to verify the clarified biomass lysate is essentially free of AAV-helper viruses. Other assays, such as Mass Spectroscopy can be used to determine the removal of flocculent.

Following aggregate removal, the AAV in the remaining biomass, e.g., clarified solution, can be further isolated, concentrated, and/or purified using techniques well known in the art, such as chromatographic purification. The capsids are recoverable from the clarified cell lysate by ion exchange chromatography, both cation and anion exchange media. Immunoaffinity chromatography medium produced with a recombinant single-chain antibody are known to bind several AAV capsid serotypes, including AAV1, AAV2, AAV6 and AAV8. The antibody can bind capsids with high specificity and affinity. 'Polishing' step including but not limited to size-exclusion, IEX, or other chromatography produces a near homogenous final AAV product. Following TFF concentration and sterile filtration, AAV produced by these methods can be used in pre-clinical studies and, with cGMP compliant practices, in clinical studies.

In some embodiments, polyethylene glycol may be used to precipitate AAV from the clarified solution. Following low-speed centrifugation, the pellet containing the AAV may be resuspended in buffer and further concentrated and purified by density gradient centrifugation, e.g. cesium chloride isopycnic gradients or iodixanol step gradients. In some embodiments, a series of filters with decreasing pore sizes are used to prevent clogging and increase the recovery of AAV. Tangential flow filtration (TFF) is a convenient technique for concentrating AAV, and also enables buffer exchange.

In some embodiments, the invention is directed to a method of isolating an adeno-associated virus (AAV) containing a target transgene, comprising: (a) providing the AAV producer cell with required DNA elements such as AAV structural/replic elements, transgene and an AAV-helper virus to generate producer cells; (b) culturing said transfected producer cell; (c) lysing said transfected producer cell to create an aqueous biomass; (d) introducing a polydiallyldialkylammonium salt into said biomass to produce an aggregate comprising said AAV-helper virus and a clarified solution comprising the AAV; and (e) processing said clarified solution with a purification column to produce isolated AAV.

In some embodiments, the invention is directed to a method of isolating an adeno-associated virus (AAV) containing a target transgene, comprising: (a) transfecting a producer cell with the AAV and an AAV-helper virus to produce transfected producer cell; (b) culturing said transfected producer cell to produce an aqueous biomass; (c) lysing said transfected producer cell to produce a cell lysate, wherein the cell lysate forms an aggregate comprising said AAV-helper virus and a clarified solution comprising the AAV (d); introducing polydiallyldialkylammonium salt into said biomass; and (e) contacting said clarified solution with a purification column to produce isolated AAV.

The present invention is further illustrated by the following Examples. These Examples are provided to aid in the understanding of the invention and are not to be construed as a limitation thereof.

EXAMPLES

Hereinafter, the present invention will be described in detail by means of examples. However, the following examples are given for more concretely describing the present invention and may not be construed as a limitation of the scope of the present invention.

Example 1

The isolation of purified AAV from an aqueous biomass comprising a cell lysate comprising AAV, a AAV-helper virus (Ad5), and cellular components is described below. In order to avoid operational steps and minimize product loss, controlled flocculation of the production reactor cell culture suspension using pDADMAC was used to optimize the harvest/upstream process as well as enhance downstream chromatography.

Cell lysate containing AAV and Ad5 virus was treated with 0.025% pDADMAC (EMD Millipore, catalog number 137069.0100). The cell lysate was then filtered using a Clarisolve 60 filter. FIG. 2 shows that the addition of pDADMAC to the cell lysate results in significant reduction of Ad5 titer by HPCL, i.e., no detectable Ad5 in pDADMAC treated clarified solution when compared with control (FIGS. 1 and 2).

TABLE 1

Data Summary of Filtration Tests

| Process Step | Parameters | Control Clarisolve 60 | Test Clarisolve 60/pDADMAC |
|---|---|---|---|
| Lysate | Starting Turbidity (NTU) | 189 | 717 |
| | Lysate (g) | 5929 | 2000 |
| | Ad5 Lysate Titer (E10 vp/mL) | 9.49 | ND |
| | Total vp in Lysate (E14) | 5.63 | NA |
| Clarification | Final Pressure (psi) | 16-22 | 9.80 |
| | Filtrate (g) | 6245 | 1995 |
| | Filter Load (L/m$^2$) | 73.2 | 869.6 |
| | Filtrate Turbidity (NTU) | 16.2 | 5.37 |
| | Ad5 Filtrate Titer (E10 vp/mL) | 5.95 | ND |
| | Total vp in Filtrate (E14) | 3.72 | NA |
| | Step yield (%) | 66 | NA |

These data show that pDADMAC is effective in removing Ad5 helper-virus from cell lysate where Ad5 viral clearance is desirable, such as in the generation of AAV using a producer cell line.

Example 2

To further demonstrate the feasibility of using pDADMAC in AAV recovery process (no negative impact on titers) in presence of a helper virus, cell lysates containing Ad5 with and without pDADMAC were tested by spiking with known quantities of AAV. The cell lysates from various conditions were clarified by centrifugation followed by sterile filtration and then tested for Ad5 (qPCR and HPLC) and AAV(qPCR). The data shows that AAV titers are not affected by pDADMAC at concentrations from 0.01 to 0.1%. For Ad5, although HPLC results suggest no detectable Ad5, this assay is not as sensitive as qPCR. The qPCR results showed a reduction in Ad5 titers, approximately 2-3 logs lower. In addition, there were also differences observed in Ad5 reduction based on the amount of pDADMAC used. Both, HPLC and qPCR results showed that Ad5 clearance was higher at 0.01% and 0.025% pDADMAC compared to 0.05% and 0.1% pDADMAC. The results are summarized in Table 2.

TABLE 2

Data showing AAV and Ad5 titers in production cell culture treated with pDADMAC after cell lysis clarification

| Test ID | Flocculent (%) | AAV (vp/mL) | Turbidity (NTU) | Ad GFP Titer (E10 vp/mL) by HPLC | GFP qPCR assay (vg/mL) | AAV qPCR GOI (vg/mL) |
|---|---|---|---|---|---|---|
| T1 | 0 (control) | NA | 28.5 | 9.49 | 1.17E+11 | NA |
| T2 | 0.01 | NA | 5.12 | 0 | 5.51E+08 | NA |
| T3 | 0.025 | NA | 3.63 | 0 | 2.36E+09 | NA |
| T4 | 0.05 | NA | 142 | 4.85 | 9.33E+10 | NA |
| T5 | 0.1 | NA | 190 | 4.50 | 2.02E+10 | NA |
| T6 | 0 (control) | 1.0E11 | 28.9 | 8.43 | 1.43E+11 | 4.47E+10 |
| T7 | 0.01 | 1.0E11 | 5.95 | 0 | 2.36E+09 | 4.12E+10 |
| T8 | 0.025 | 1.0E11 | 3.69 | 0 | 2.36E+09 | 4.46E+10 |
| T9 | 0.05 | 1.0E11 | 155 | 4.13 | 2.62E+09 | 4.91E+10 |
| T10 | 0.1 | 1.0E11 | 186 | 4.70 | 4.28E+10 | 3.82E+10 |

Example 3

To confirm that pDADMAC was not affecting the AAV virus in general and can be used to harvest AAV from other processes, the flocculation process was tested to AAV generated using a Baculovirus based system. In this case, AAV was produced in insect cells, and pDADMAC was added into culture lysate at 0, 0.025%, 0.050% and 0.1%. AAV in each sample was analyzed by qPCR (Table 3). As expected, no difference in AAV titers was observed between the control samples and the samples harvested using pDADMAC.

TABLE 3

Effect of pDADMAC on AAV qPCR titers when using Baculovirus based AAV production

| Sample tested | Flocculent conc. (pDADMAC) | AAV Titer by qPCR vg/mL |
|---|---|---|
| control | N/A | 2.39E+11 |
| Trial 1 | 0.025 | 2.23E+11 |
| Trial 2 | 0.05 | 2.26E+11 |
| Trial 3 | 0.1 | 2.38E+11 |

Example 4 pDADMAC was also tested in a Baculovirus system with a recombinant Baculovirus (rBV). Culture lysate with 0, 0.025% and 0.1% pDADMAC were tested. Recombinant Baculovirus (rBV) in each sample was tested in pDADMAC treated and untreated (harvested using standard filters—control) samples using an infectious titer assay (BacPAK), and results are summarized in Table 4. Data obtained in this experiment showed that rBV infectious titers were not affected when pDADMAC for harvesting compared to the standard procedure.

TABLE 4

Impact of pDADMAC on baculovirus titer

| Sample Tested | Flocculent conc. (pDADMAC) | BacPAK titer (IFU/mL) |
|---|---|---|
| Control | N/A | 7.73E7 |
| Trial 1 | 0.025% | 6.32E7 |
| Trial 2 | 0.1% | 7.77E7 |

In conclusion, it appears that use of pDADMAC as a flocculant was able to safely remove Ad5 helper virus (to below LOD by HPLC) used in producer cell line processes without impacting target AAV titers (Table 3). Similarly, AAV titer produced in rBV-based systems is also not impacted by use of pDADMAC flocculant (Table 4).

CONCLUSION

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A method of purifying adeno-associated virus (AAV) from an aqueous biomass containing said adeno-associated virus and at least one AAV-helper virus, comprising:
   a. contacting said biomass with a polydiallyldialkylammonium salt to form an aggregate and a clarified solution, wherein said aggregate comprises said at least one AAV-helper virus,
   b. removing said aggregate from the clarified solution, and
   c. further isolating the AAV from the clarified solution.

2. The method of claim 1, wherein the clarified solution is significantly reduced in the AAV-helper virus.

3. The method of claim 1, wherein the polydiallyldialkylammonium salt is polydiallyldimethylammonium salt.

4. The method of claim 1, wherein the polydiallyldialkylammonium salt is polydiallyldimethylammonium chloride (pDADMAC).

5. The method of claim 1, wherein said at least one AAV-helper virus is selected from adenovirus, herpes simplex virus or baculovirus.

6. The method of claim 2, wherein said at least one AAV-helper virus is adenovirus.

7. The method of claim 2, wherein said at least one AAV-helper virus is baculovirus.

8. The method of claim 1, wherein said biomass is a cell lysate.

9. The method of claim 1, wherein said polydiallyldialkylammonium salt is present in said biomass at a concentration of between 0.01% and 0.5% (w/v).

10. A method of isolating an adeno-associated virus (AAV) containing a target transgene, comprising:
    a. transfecting a producer cell with the AAV and an AAV-helper virus to produce transfected producer cell;
    b. culturing said transfected producer cell;
    c. lysing said transfected producer cell to create an aqueous biomass;
    d. introducing polydiallyldialkylammonium salt into said biomass to produce an aggregate comprising said AAV-helper virus and a clarified solution comprising the AAV; and
    e. contacting said clarified solution with a purification column to produce isolated AAV.

11. A method of isolating an adeno-associated virus (AAV) containing a target transgene, comprising:
    a. transfecting a producer cell with the AAV and an AAV-helper virus to produce transfected producer cell;
    b. culturing said transfected producer ceil to produce an aqueous biomass;
    c. introducing polydiallyldialkylammonium salt into said biomass; and
    d. processing said clarified solution with a purification column to produce isolated AAV.

12. The method of claim 11, wherein said AAV-helper virus is selected from the group consisting of adenovirus, herpes simplex virus and baculovirus.

13. The method of claim 11, wherein the polydiallyldialkylammonium salt is polydiallyldimethylammonium salt.

14. The method of claim 11, wherein the polydiallyldialkylammonium salt is polydiallyldimethylammonium chloride (pDADMAC).

15. The method of claim 11, wherein said AAV-helper virus is adenovirus.

16. The method of claim 11, wherein said AAV-helper virus is baculovirus.

17. The method of claim 11, wherein said producer cell line is a He La cell line, CHO cell line, an HEK293 cell, or a *Spodoptera frugiperda* (Sf9) cell line.

18. The method of claim 11, further comprising contacting said producer cell with an additional genetic element required to assemble AAV.

19. The method of claim 18, wherein said genetic element is selected from the group consisting of AAV non-structural proteins, AAV structural proteins and cellular factors necessary for macromolecular synthesis.

20. The method of claim 11, wherein the AAV comprises a transgene.

* * * * *